United States Patent
Wei et al.

(10) Patent No.: US 11,846,546 B1
(45) Date of Patent: Dec. 19, 2023

(54) ENHANCED FULL RANGE OPTICAL COHERENCE TOMOGRAPHY

(71) Applicant: Topcon Corporation, Tokyo (JP)

(72) Inventors: Xiang Wei, San Jose, CA (US); Tony Ko, Cupertino, CA (US)

(73) Assignee: TOPCON CORPORATION, Tokyo (JP)

( * ) Notice: Subject to any disclaimer, the term of this patent is extended or adjusted under 35 U.S.C. 154(b) by 0 days.

(21) Appl. No.: 17/814,615

(22) Filed: Jul. 25, 2022

(51) Int. Cl.
*G01J 3/453* (2006.01)
*G01J 3/28* (2006.01)

(52) U.S. Cl.
CPC ............. *G01J 3/453* (2013.01); *G01J 3/2823* (2013.01); *G01J 2003/4538* (2013.01)

(58) Field of Classification Search
CPC ... G01N 2021/1787; G01J 3/2823; G01J 3/45
See application file for complete search history.

(56) References Cited

U.S. PATENT DOCUMENTS

| | | |
|---|---|---|
| 4,984,893 A | 1/1991 | Lange |
| 8,180,134 B2 | 5/2012 | Wang |
| 2005/0185685 A1 | 8/2005 | Chapman et al. |
| 2008/0002183 A1 | 1/2008 | Yatagai et al. |

FOREIGN PATENT DOCUMENTS

WO 2007121175 A2 10/2007

OTHER PUBLICATIONS

Bernhard Baumann, "Simple technique for full-range complex spectral domain optical coherence tomography", SPIE, 2008 (Year: 2008).*
Miao Zhang, "Three-Dimensional Full-Range Dual-Band Fourier Domain Optical Coherence Tomography Accelerated by Graphic Processing Unit", 2018, Ruikang K Wang (Year: 2018).*
Ruikang K Wang, "Fourier domain optical coherence tomography achieves full range complex imaging in vivo by introducing a carrier frequency during scanning", 2007 (Year: 2007).*
Yong Huang, "In-vivo gingival sulcus imaging using full-range, complex-conjugate-free, endoscopic spectral domain optical coherence tomography", 2012 (Year: 2012).*
Schmit et al., "Extended averaging technique for derivation of error-compensating algorithms in phase-shifting interferometry"; Applied Optics, vol. 34, No. 19, pp. 3610-3619. Jul. 1, 1995.
Wojtkowski et al., "Full range complex spectral optical coherence tomography technique in eye imaging"; Optics Letters, vol. 27, No. 16, pp. 1415-1417. Aug. 15, 2002.
Wang, "In vivo full range complex Fourier domain optical coherence tomography"; Applied Physics Letters, vol. 90, p. 054103-1-054103-3, (2007).

(Continued)

*Primary Examiner* — Maurice C Smith
(74) *Attorney, Agent, or Firm* — Pearne & Gordon LLP

(57) ABSTRACT

A full-range imaging method doubles imaging range of conventional techniques by removing mirror images of an imaged object that limit conventional images to a "half-range" and that are caused in part by the loss of phase information in a detected signal. Phase information of the detected signal is reconstructed with an averaging technique based on a modulated phase induced in the detected signal during scanning.

16 Claims, 11 Drawing Sheets

(56) References Cited

OTHER PUBLICATIONS

Baumann et al., "Full range complex spectral domain optical coherence tomography without additional phase shifters", Optics Express, vol. 15, No. 20, pp. 13375-13387, Oct. 1, 2007.
Yasuno et al., "High speed full-range Fourier demain optical coherence tomography by simultaneous B-M-mode scanning", Proceedings of SPIE, Coherence Domain Optical Methods and Optical Coherence Tomography in Biomedicine IX, vol. 5690, 2005, pp. 137-142, doi: 10.1117/12.589061, Archive # 000109317.
Yasuno et al., "Simultaneous B-M-mode scanning method for real-time full-range Fourier domain optical coherence tomorgraphy", Applied Optics, vol. 45, No. 8, Mar. 10, 2006, pp. 1861-1865, XP002712844, ISSN: 0003-6935.
Yasuno et al., "Real time and full-range complex Fourier domain optical coherence tomography", Optical and Quantum Electronics, vol. 37, 1157-1163, 2005, DOI 10.1007/s11082-005-4186-5.
European Search Report for European Application No. 22 19 1476 dated May 23, 2023.

\* cited by examiner

ENHANCED FULL RANGE OPTICAL COHERENCE TOMOGRAPHY

BACKGROUND

Optical coherence tomography (OCT) is a non-invasive imaging technique, often used in ophthalmology. OCT relies on principles of interferometry to image and collect information about an object (such as the eye of a subject). Particularly, light from a source is split into a sample arm where it is reflected by the object being imaged, and a reference arm where it is reflected by a reference object such as a mirror. The reflected lights are then optically combined in a detection arm in a manner that produces an optical signal having an interference pattern that is captured by a spectrometer, photodiode(s) or the like. The detected optical signal is processed to reconstruct the object and generate OCT images.

The optical signal detected by the OCT system contains an amplitude part and a phase part. However, the cameras of spectrometers only capture the amplitude part of the optical signal. The phase part of the optical signal is thus lost and the OCT image is reconstructed using only the amplitude part.

Due to lack of phase signal, the reconstructed OCT image has a complex conjugated mirror image. With reference to FIGS. 1A and 1B, these two images are symmetric with respect to the center peak, known as the DC line. In instances where the images cross the DC line, they may overlap. Due to the image mirroring, only half of the image range ("half-range" OCT images) can be used.

While some techniques have been developed to remove the mirrored image and double the useable imaging range (thus utilizing a "full-range" of the OCT image), those techniques suffer from some deficiencies. For example, techniques that use a piezo stage have a very limited travel range, which limits a phase tuning range and may not be sufficient for widefield imaging. Further, piezo stages can be expensive. Techniques that offset an incident light beam from the center of a galvo scanner can only work with a fixed scan pattern. Further, these techniques can require high density scans that increase scan time and required processing power.

BRIEF SUMMARY

According to one example of the present disclosure, an imaging system comprises: a light source and a spectrometer in an interferometric arrangement; a phase modulator configured to adjust a phase of light detected by the spectrometer by inducing a positive phase modulation that increases the phase and inducing a negative phase modulation that decreases the phase; and a processor configured to: reconstruct a phase of a signal detected by the spectrometer based on the adjusted phase, and generate a full-range image based on an amplitude of the signal detected by the spectrometer and the reconstructed phase, wherein the positive phase modulation and the negative phase modulation are each induced at least once during a single B-scan.

In various embodiments of the above example, the phase modulator is controlled according to a triangular waveform; the phase modulator is a phase galvo comprising a rotatable glass; the glass is configured to rotate linearly during at least part of a B-scan; the glass is configured to rotate during the B-scan according to a triangular waveform; the phase modulator is a photonic integrated circuit; the processor is configured to separately reconstruct the phase of the signal detected by the spectrometer based on the induced positive phase modulation and the induced negative phase modulation, thereby generating a positively-tuned image and a negatively-tuned image, and the processor is configured to generate the full-range image by combining the positively-tuned image and the negatively-tuned image; the system further comprises: scanning optics configured to scan an object being imaged by the interferometric arrangement along a fast scanning axis, wherein the scanning optics are configured to repeat a scan of a portion of the object along the fast scanning axis when the phase modulator changes between inducing the positive phase modulation and the negative phase modulation; the phase modulator is in a sample arm of the interferometric arrangement; the phase modulator is in a reference arm of the interferometric arrangement; and/or the phase modulator is configured to adjust the phase by $\pi/2$ between each A-line of the single B-scan.

According to another example of the present disclosure, an imaging method comprises: scanning an object with an incident light with an interferometric imaging system; optically modulating a phase of an interference signal from the interferometric imaging system; detecting the optically modulated interference signal; reconstructing a phase of the detected signal based on the modulated phase by determining a representative phase based on at least four A-lines or B-scans; and generating a full-range image based on an amplitude of the detected signal detected and the reconstructed phase.

In various embodiments of the above example, optically modulating the phase comprises inducing a positive phase modulation and a negative phase modulation in a single B-scan, the phase is separately reconstructed based on the positive phase modulation and the negative phase modulation adjusted phase, the method further comprises generating a positively-tuned image based on the reconstructed phase of the positive phase modulation, and generating a negatively-tuned image based on the reconstructed phase of the negative phase modulation, and generating the full-range image comprises combining the positively-tuned image and the negatively-tuned image; optically modulating the phase comprises inducing a by $\pi/2$ phase between each A-line and/or B-scan; optically modulating the phase comprises rotating a phase galvo according to a triangular waveform; optically modulating the phase comprises switching light paths through a photonic integrated circuit; and/or generating the full-range image comprises performing a Fourier transform on a complex signal, a real part of the complex signal is represented by at least two of the at least four A-lines or B-scans, and an imaginary part of the complex signal is represented by a different at least two of the at least four A-lines or B-scans, and the A-lines or B-scans representing the real and imaginary parts of the complex signal are determined based on the reconstructed phase.

DETAILED DESCRIPTION OF THE DRAWING

Figure 1A:
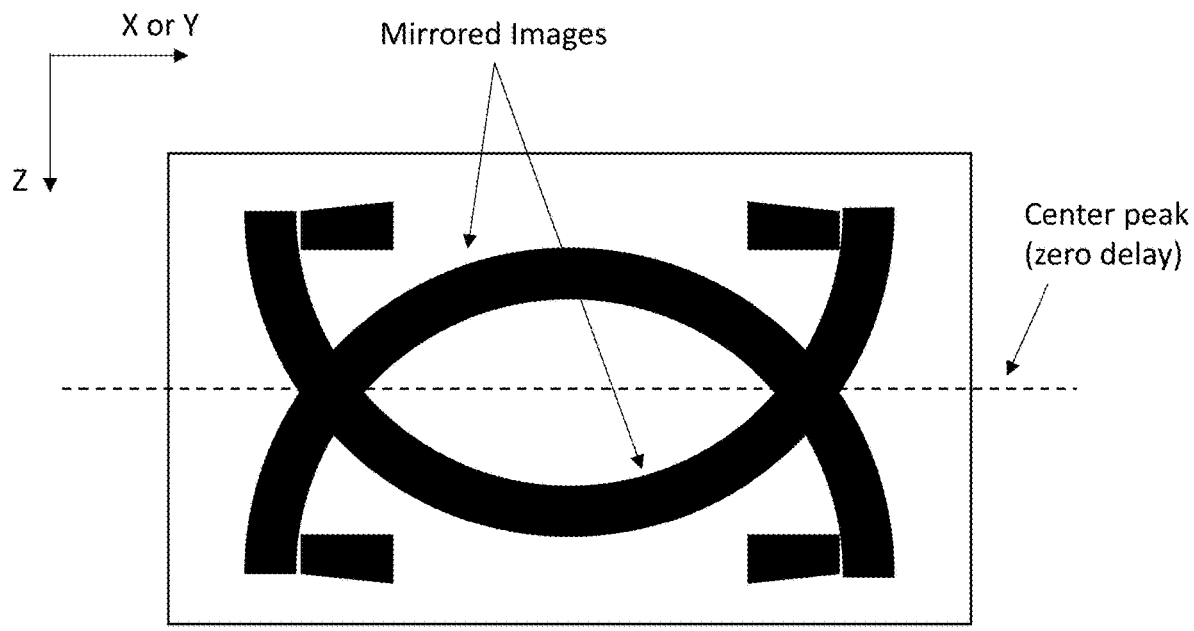
FIG. 1A conceptually illustrates an example conventional "half-range" image.
Figure 1B:
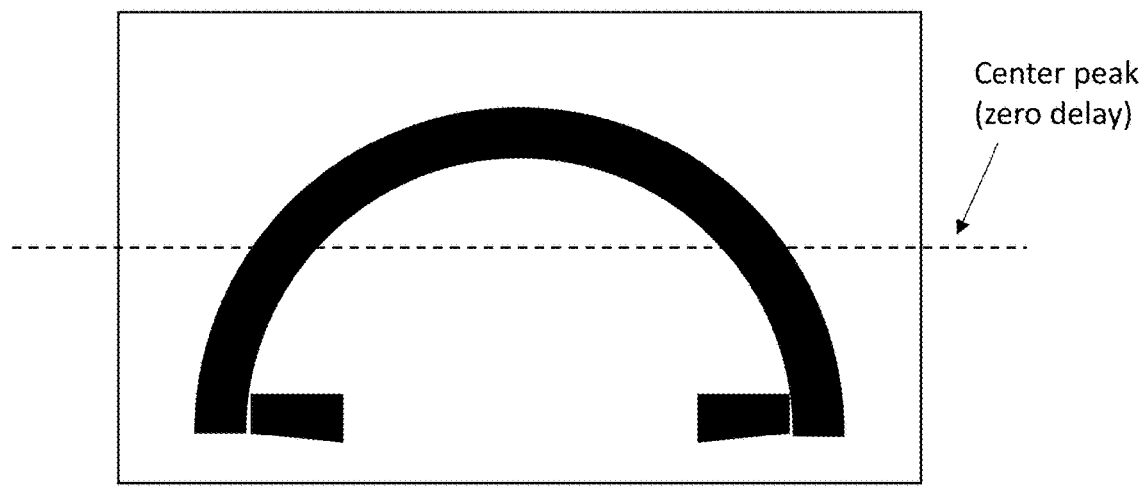
FIG. 1B conceptually illustrates an example conventional "full-range" image.
Figure 2A:
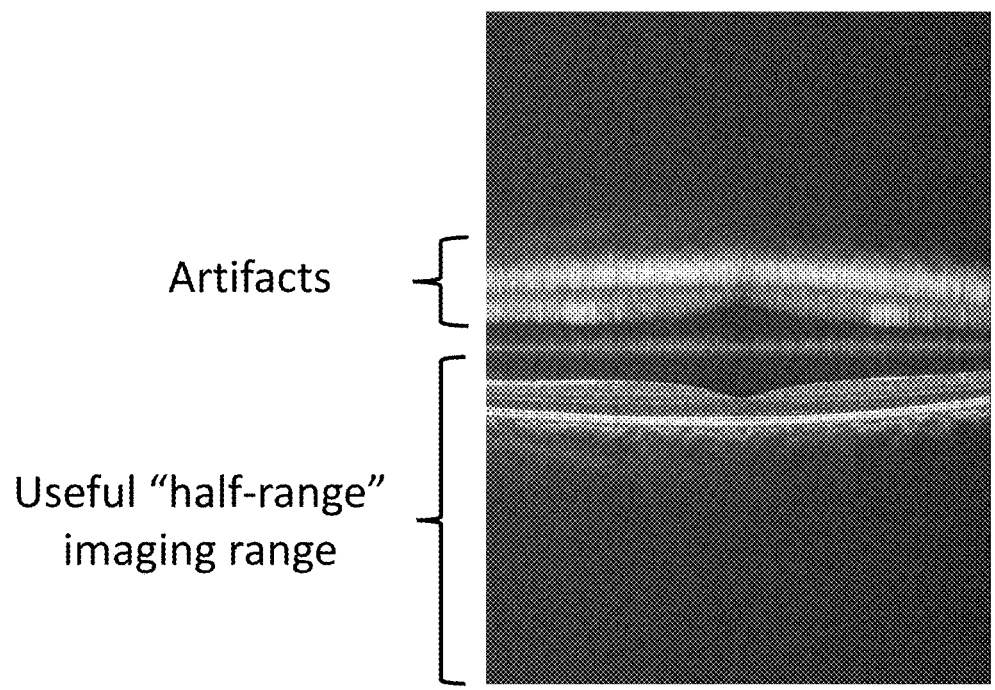
FIG. 2A is an example conventional "half-range" OCT image.
Figure 2B:
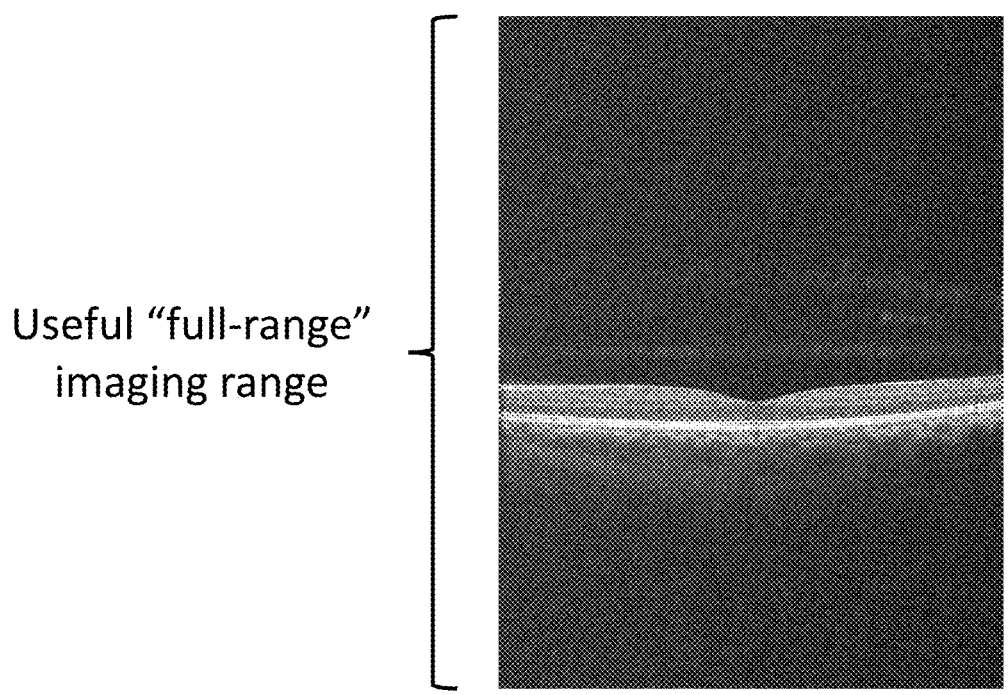
FIG. 2B is an example "full-range" OCT image according to the present disclosure.

Based on the foregoing, the present disclosure relates to full-range OCT imaging without the deficiencies in current technologies. With reference to FIGS. 2A and 2B, according to the present disclosure complex conjugate artifacts (mirror images) associated with conventional half-range OCT images (FIG. 2A) can be mitigated or eliminated to double the imaging depth range to produce "full-range" OCT images (FIG. 2B). This can be accomplished without a high density scan and the tuning range limitations associated with existing techniques, and in a more compact and cost-effective manner.

Figure 3:
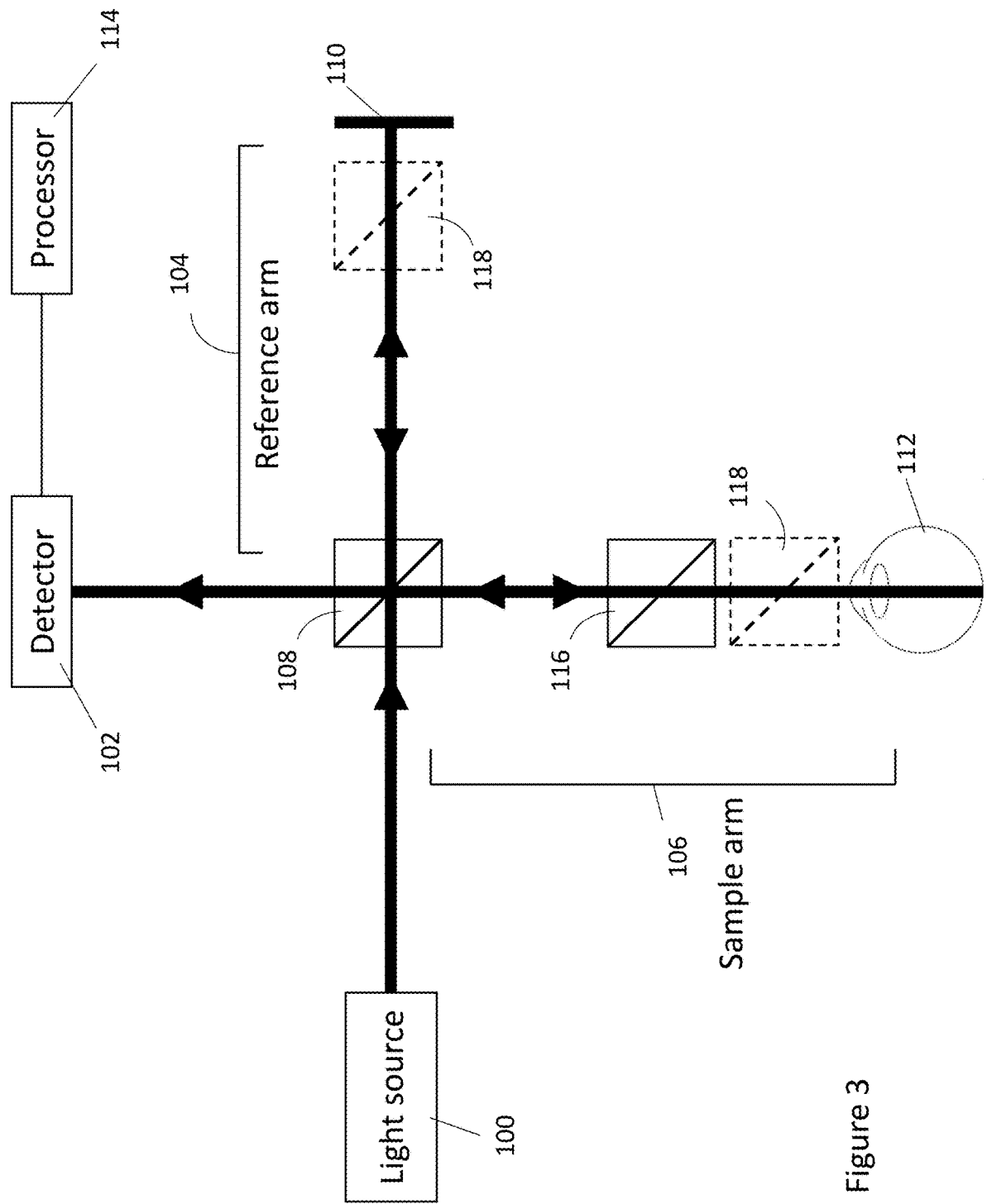
FIG. 3 illustrates an example schematic of an optical coherence tomography system.

FIG. 3 illustrates an example OCT system. As seen therein, the system includes a light source 100. The light generated by the light source 100 is split by, for example, a beam splitter (as part of optics 108), and sent to a reference arm 104 and a sample arm 106. The light in the sample arm 106 is backscattered or otherwise reflected off an object, such as the retina of an eye 112. The light in the reference arm 104 is backscattered or otherwise reflected, by a mirror 110 or like object. Light from the sample arm 104 and reference arm 106 is recombined at the optics 108 and a corresponding interference signal is detected by a detector 102. The detector 102, such as a spectrometer, outputs an electrical signal corresponding to the interference signal to a processor 114, where it may be stored and processed into OCT signal data. The processor 114 may then further generate corresponding images or otherwise perform analysis of the data. The processor 114 may also be associated with an input/output interface (not shown) including a display for outputting processed images, or information related to the analysis of those images. The input/output interface may also include hardware such as buttons, keys, or other controls for receiving user inputs to the system. In some embodiments, the processor 114 may also be used to control the light source and imaging process.

OCT signal data collected at a single location (e.g., an X-Y point) is referred to as an A-line (containing information in the Z depth direction at the X-Y location). Scanning optics 116 then progress incident light from the light source 100 along a scanning pattern on the imaged object to collect two-dimensional or three-dimensional data of the object. For example in a traditional scanning pattern, A-lines are sequentially captured along a fast scanning axis (either the X or Y direction); then when the system reaches the end of the fast imaging axis, scanning progresses one step along a slow scanning axis (the other of the X or Y direction) and repeats capturing along the fast scanning axis. This continues until a desired volume of data is captured. Of course other scanning patterns may be employed by the scanning optics 116. A collection of A-lines along the fast scanning axis at a point on the slow scanning axis (e.g., in the X-Z or Y-Z plane), or vice versa, is referred to as a B-scan In order to obtain the phase part of the optical signal to generate full-range OCT images, a tunable frequency (a phase modulation signal) is added to the optical signal by a phase modulator 118. As shown in FIG. 3, the phase modulator 118 may be implemented as its own element in the reference arm 104 or the sample arm 106. However, it should be understood that the phase modulator 118 may be integrated with or otherwise part of optics 108, as part of scanning optics 116, or otherwise part of the reference arm 104 and/or sample arm 106. Further, the phase modulator 118 may be included before or after scanning optics 116 within the sample arm 106. The phase modulator 118 adjusts the phase of the optical signal by controlling the optical path length of the optical signal. Preferably, the phase modulator 118 induces a $\pi/2$ phase change between each A-line and/or each B-scan.

Figure 4:
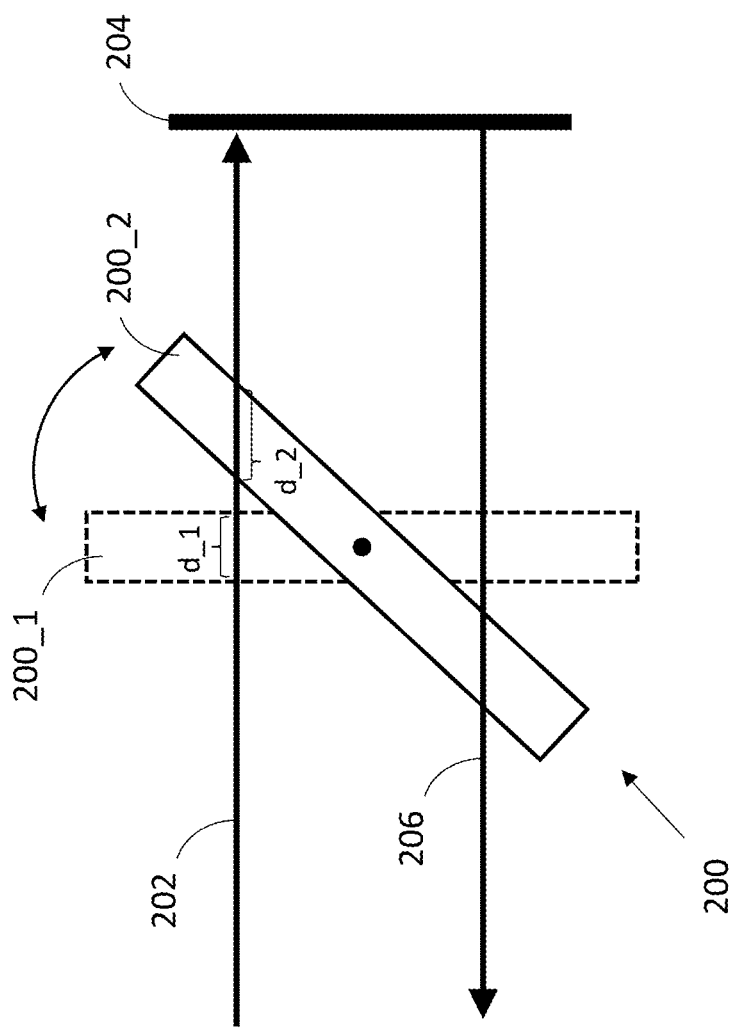
FIG. 4 illustrates an example phase galvo.

According to one embodiment illustrated in FIG. 4, the phase modulator 118 is a glass 200 with a known thickness (a phase galvo) that is rotated by a galvo motor or like actuator according to a control signal. As seen in the figure, light 202 enters the phase galvo, is reflected by an element 204 (e.g., reference mirror if the phase modulator 118 is in the reference arm 104, or the object 112 if the phase modulator 118 is in the sample arm 106), and light 206 exits the phase galvo. The entering light 202 and exiting light 206 each pass through the glass 200 along a path length dependent on the rotation angle of the glass. For example, the glass 200 of the phase galvo is shown at a first position 200_1 (90 degrees with respect to lights 202, 206) where a path length therethrough is equal to the thickness d_1 of the glass 200. In contrast, the path length d_2 through the glass 200 at a second position 200_2 (45 degrees with respect to lights 202, 206) is greater than the width d_1 of the glass 200. The different path lengths d_1, d_2 take a different amount of time for light to pass through. Therefore, as the glass 200 is rotated, a delay (the phase modulation signal) is induced in the lights 202, 206, and thus the resulting optical signal. It should be understood that the relative positions of lights 202, 206 are illustrative only, and that light can both enter and exit the phase modulator along the entire length of glass 200.

Because the glass 200 is rotated (i.e., adjusted circularly), the path length change through a glass 200 having a constant thickness is not linear. In other words, the change in path length through the glass 200 is not linearly related to an angle of rotation of the glass 200. As a result, the phase modulation signal induced by such a phase galvo is not constant. In other words, the difference in phase induced by a phase galvo at any two positions (i.e., caused by rotation of the phase galvo) is not the same.

Particularly, the optical path of a tilted glass is given as:

$$d = n \cdot \frac{d1}{\tan(\theta)}$$

where d is the optical path in the glass, n is the reflective index of the glass, d1 is the thickness of the glass, and θ is the tilted angle. The path difference between adjacent positions (e.g., between adjacent A-lines or B-scans) is thus given as:

$$\Delta d = n \cdot \left( \frac{d1}{\tan(\theta)} - \frac{d1}{\tan(\theta + \Delta\theta)} \right)$$

where $\Delta\theta$ is the phase galvo rotation angle difference between adjacent positions (the phase galvo angle correlated to one position being $\theta$, and correlated to another position being $\theta+\Delta\theta$). Assuming the phase galvo glass is rotated around 45° and the rotation angle between adjacent positions is small, the path difference between adjacent positions can be simplified to:

$$\Delta d = n \cdot \sqrt{2} \cdot d1 \cdot \Delta\theta$$

Figure 5A:
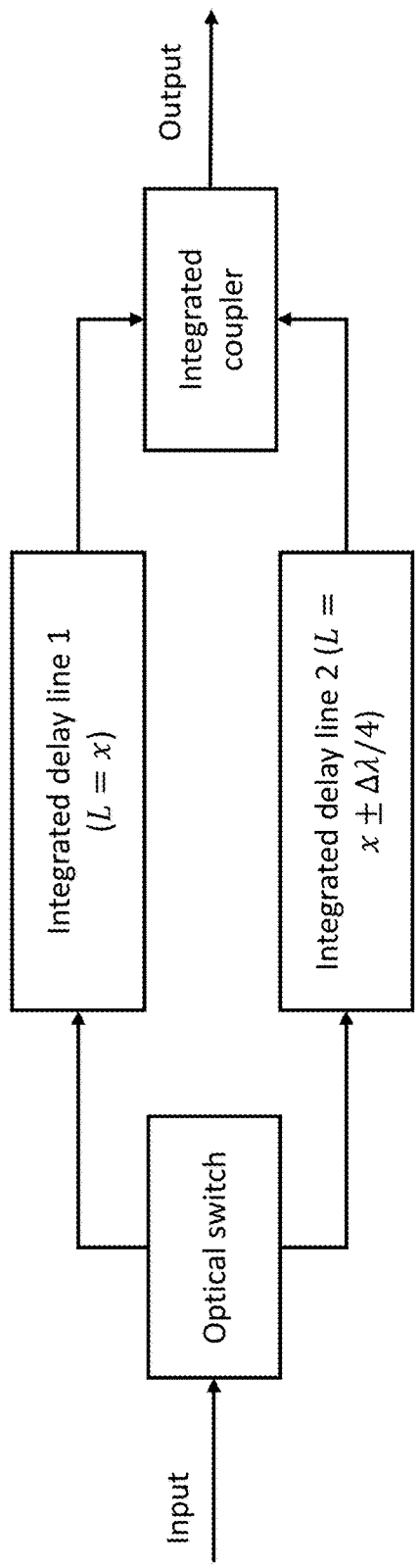
FIGS. 5A and 5B schematically illustrate example photonic integrated circuits.
Figure 5B:
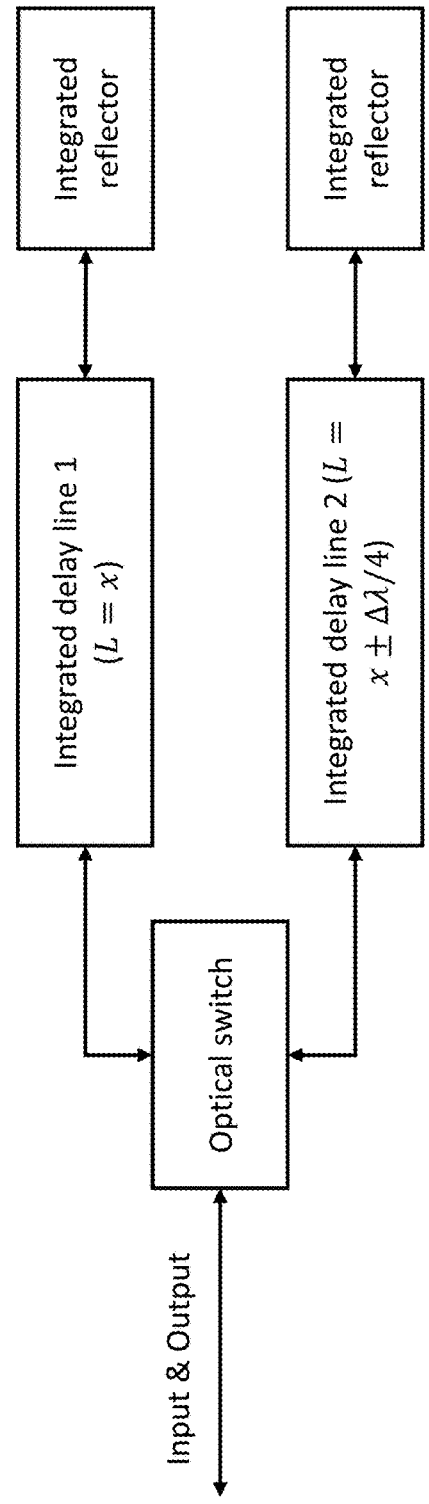

According to another embodiment, the phase modulator 118 may be an optical delay line in a photonic integrated circuit (PIC), such as that illustrated in FIGS. 5A and 5B. As above, the PIC for the phase modulator may be a distinct element, or integrated with optics 108 or scanner 116. When using a PIC, the control signal may be a digital signal supplied to the PIC that switches an optical path therethrough between two lines having different lengths. In the examples of FIGS. 5A and 5B, light is input to an optical switch, which is controlled by the modulation signal. The optical switch selectively pass the input light to either integrated delay line 1 (having a path length x) or an integrated delay line 2 (having a path length x±Δλ/4, that is, a quarter of the center wavelength of light passing therethrough). In the example of FIG. 5A, the delay lines are coupled by an integrated coupler, and light is output from the integrated coupler. In the example of FIG. 5B, light in each delay line is reflected by an integrated reflector, traverses the integrated delay line a second time, and is output from the optical switch.

It should be understood that the delays of each integrated delay line may be different than those noted in FIGS. 5A and 5B. For example, because light is reflected in the embodiment of FIG. 5B and traverses each delay line twice, the length of each line may be half of the desired length/delay. For example, the length of integrated delay line 1 of FIG. 5B may be equal to x, and the length of integrated delay line 2 may be equal to x+Δλ/4. In some embodiments, the difference in path lengths between the delay lines may be greater or less than one quarter of the center wavelength. Further, more than two delay lines may be implemented in a PIC.

The phase modulation signal is tuned according to a waveform at a specific frequency and amplitude, the waveform being applied as a control for the phase modulator 118 or as the induced phase modulation itself. As discussed with respect to the below examples, the waveform may take the form of a sawtooth, step-wise, triangular, or like pattern. Generally, waveform is determined to maximize an extinction ratio of full range OCT images, thereby minimizing the complex conjugate artifact/mirror image. In other words, the extinction ratio may be defined as a ratio between the signal and the complex conjugate artifact, or the like, where minimizing the amount of artifact maximizes the ratio. FIG. 6A-6D illustrate various phase galvo control signals (for controlling a phase galvo phase modulator 118) and fast scanning galvo control signals (for controlling the scanning optics 116 in the fast imaging axis), for inducing phase modulation signals according to different examples of the present disclosure.

Figure 6A:
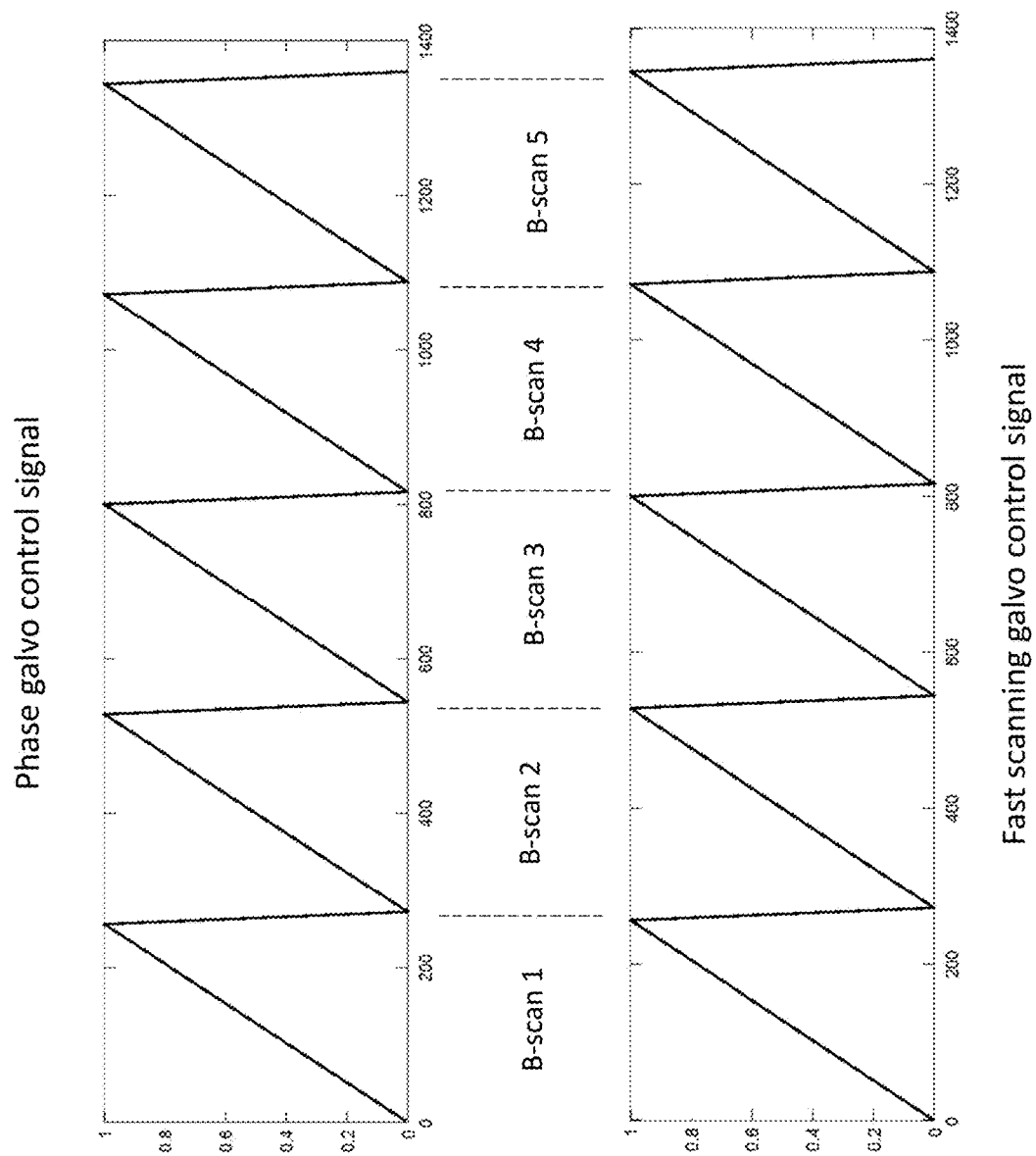
FIG. 6A illustrates example phase and fast scanning galvo control signals for inducing a first example phase modulation.

According to a first example illustrated in FIG. 6A, the phase galvo control signal causes a constant rotation of the phase galvo (or change in delay lines in a PIC) during each B-scan (one period of the fast scanning galvo control signal). This produces an intra-B-scan modulation. Within each B-scan, the phase galvo control signal causes a constant rotation of the phase galvo. In other words, the change in angle between adjacent A-lines of the B-scan is constant throughout the entirety of the B-scan. In this example, the phase galvo signal mirrors the fast scanning galvo control signal, which each have sawtooth waveforms.

Figure 6B:
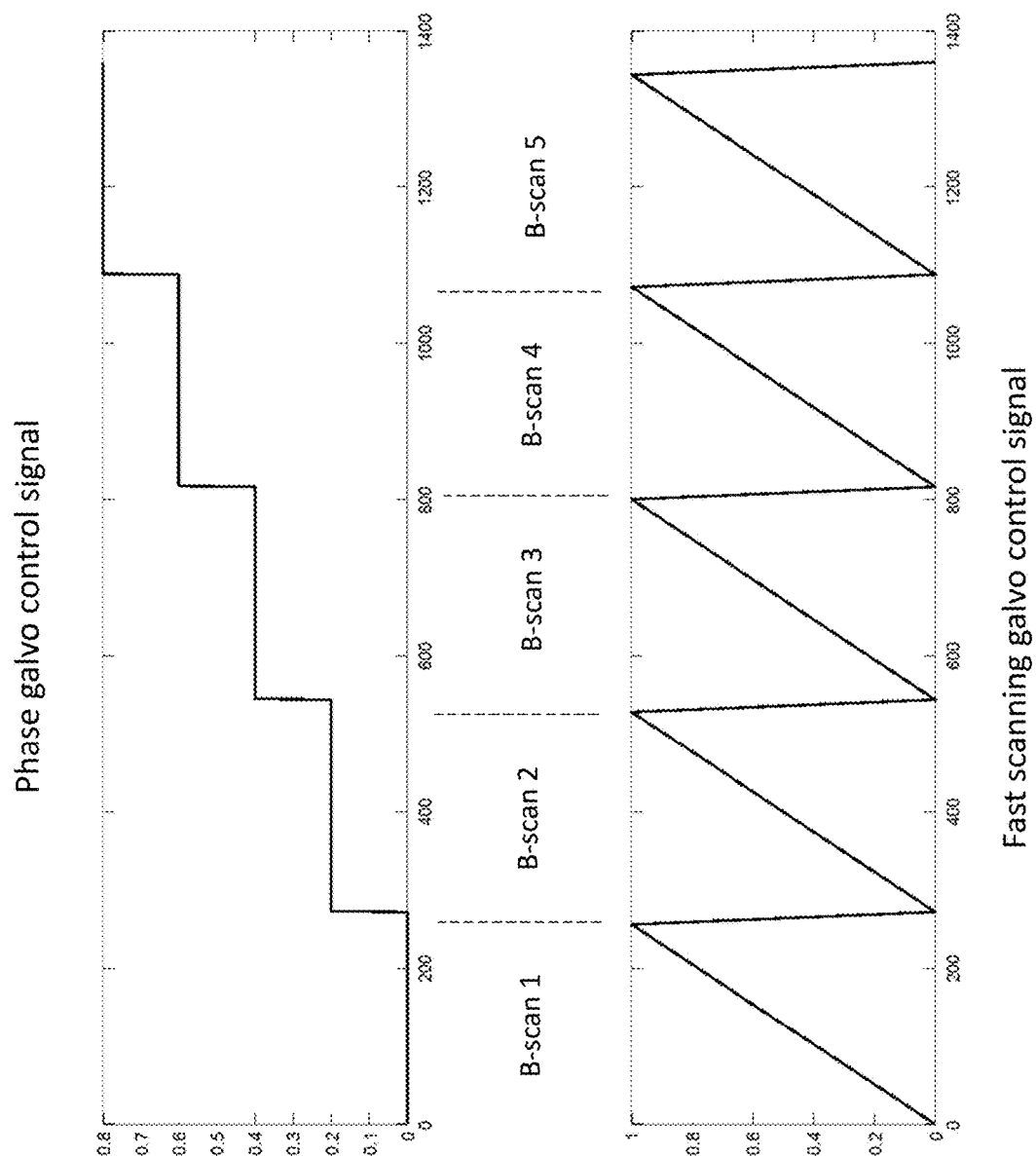
FIG. 6B illustrates example phase and fast scanning galvo control signals for inducing a second example phase modulation.

In contrast, phase galvo control signal in the example illustrated in FIG. 6B only changes between B-scans. This produces an inter-B-scan modulation. In other words, according to the example of FIG. 6B, the same phase modulation is induced for every A-line in a single B-scan (e.g., along the fast scanning axis at one scan point on the slow moving axis). As the scanning pattern reaches the end of the fast scanning axis, the phase galvo is rotated (or the delay line is switched in a PIC) so that a different phase modulation signal is introduced in the next B-scan. Such a phase galvo control corresponds to a step-wise pattern.

Figure 6C:
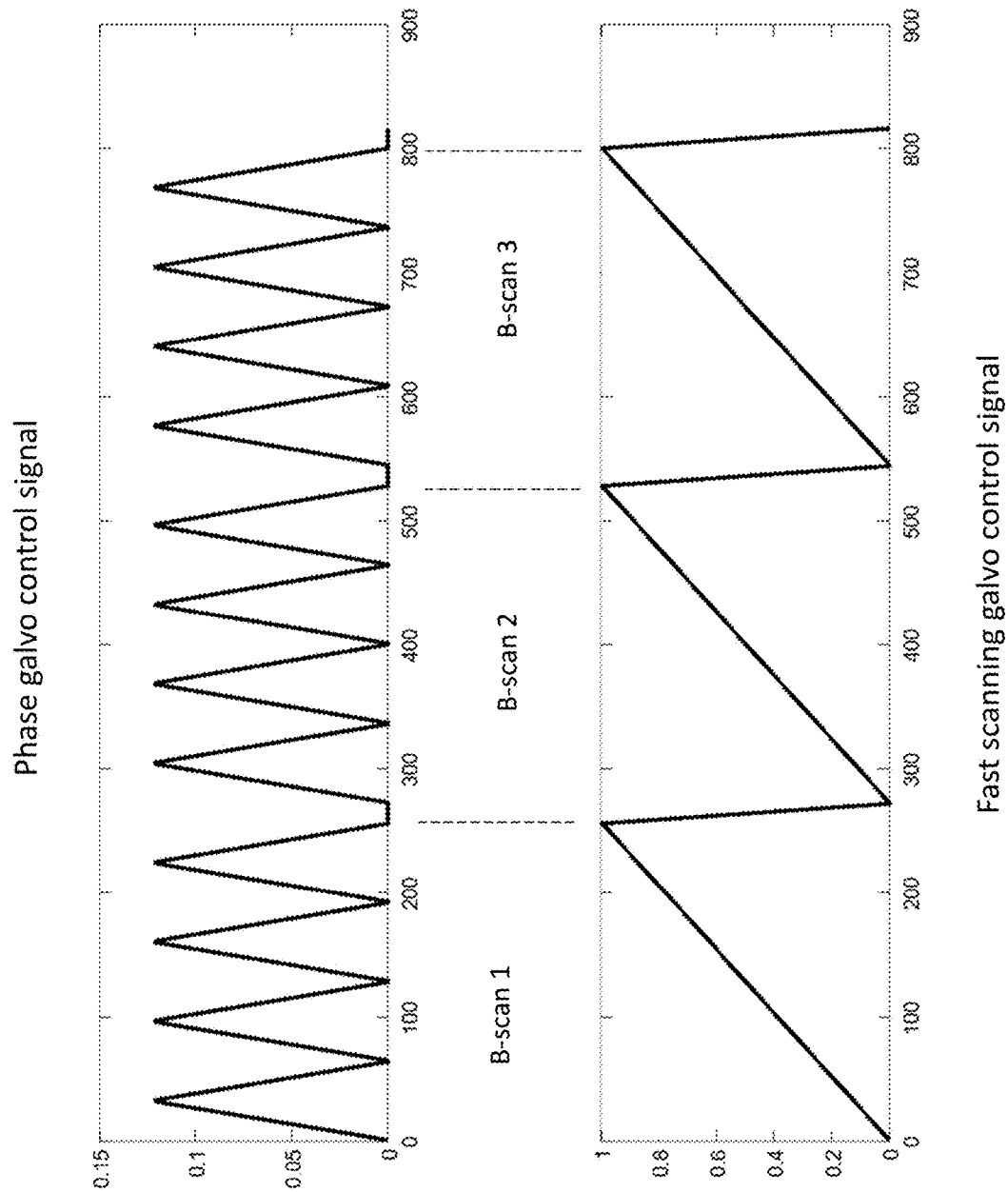
FIG. 6C illustrates example phase and fast scanning galvo control signals for inducing a third example phase modulation.

The example of FIG. 6C illustrates a triangular waveform. As with the example of FIG. 6A, the waveform of FIG. 6C induces an intra-B-scan modulation. However, in contrast to the example of FIG. 6A, the phase galvo rotation reverses direction one or more times during the B-scan. For example, the phase galvo may be rotated in one direction (a positive sloping phase galvo control signal) for a first portion of the A-lines in the B-scan (e.g., half of the A-lines), and then rotated in the reverse direction (a negative sloping phase galvo control signal) for the second remaining portion of A-lines in the B-scan. In other words, the phase galvo may be rotated back and forth within one B-scan. Where the phase modulator 118 is a PIC, this effect can be accomplished by sequentially switching through delay lines having increasing path lengths/delays for the first portion of A-lines, and then sequentially reversing back through those delay lines successively decreasing the path lengths/delays for the second remaining portion of A-lines. Generally, an increasing delay is said to produce a positive phase modulation signal, whereas a reversed or decreasing delay is said to produce a negative phase modulation signal. Thus, the example of FIG. 6C introduces at least one positive phase modulation signal and at least one negative phase modulation signal. The phase modulation protocol of the example in FIG. 6C can improve the tuning range and avoid the tuning range limitation in wide-field imaging.

Figure 6D:
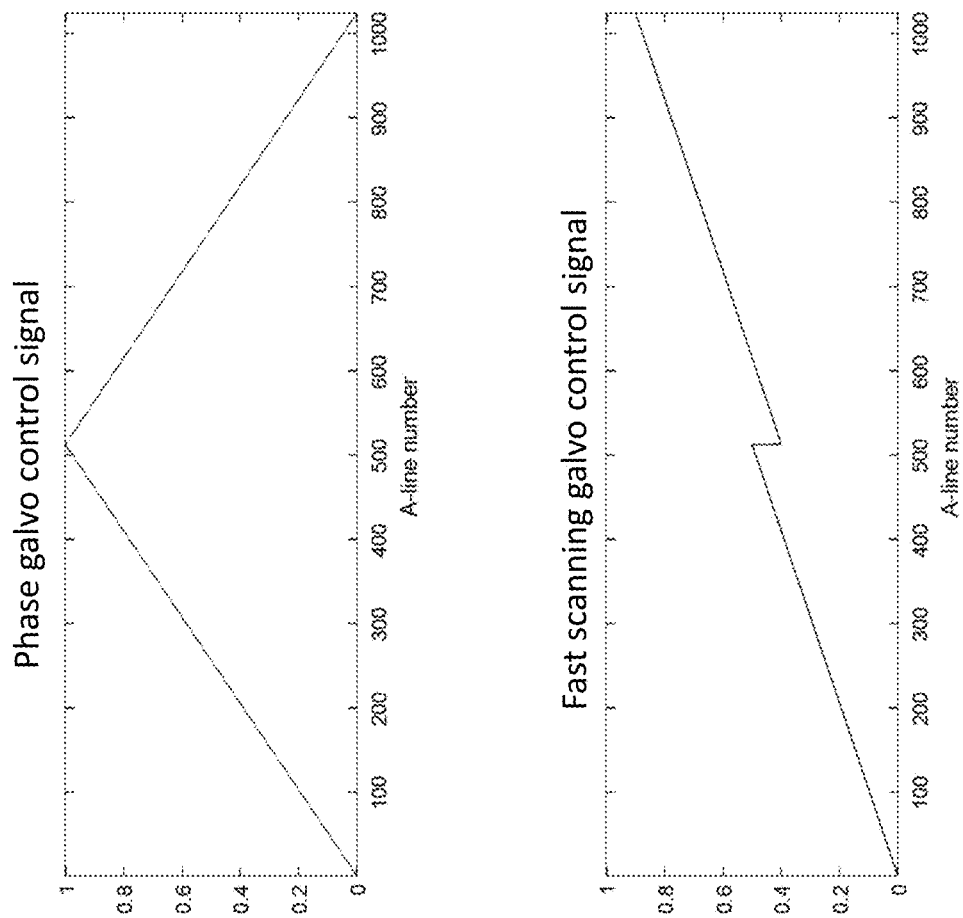
FIG. 6D illustrates example phase and fast scanning galvo control signals for inducing a fourth example phase modulation.

Artifacts may be introduced when the phase modulation signal is reversed (e.g., from positive to negative). These artifacts may be removed or mitigated by reversing scanning in the fast scanning direction when the phase modulation signal is reversed. Such a scanning protocol is illustrated in the example of FIG. 6D. As seen in FIG. 6D, scanning in the fast scanning direction returns a predetermined number of A-lines (e.g., 64 A-lines) and then restarts scanning when the phase modulation signal changes direction. In other words, the A-lines scanned while the phase galvo changes direction are re-scanned following the change in direction. More particularly as seen in FIG. 6D, the phase galvo control signal increases for the first 512 A-lines of a B-scan, thereby rotating the phase galvo in a first direction. During this time, the fast scanning galvo control signal is also increased to progress scanning along the fast scanning axis. The phase galvo control signal is then decreased for the remaining 512 A-lines of the B-scan, thereby reversing direction of the phase galvo to its starting position. When the phase galvo is reversed, the fast scanning galvo control signal is decreased to return the scanner the equivalent of 64 A-lines. Scanning is then allowed to progress in the fast scanning direction again until 1024 A-lines are captured.

While the example of FIG. 6D only illustrates one change in direction during a B-scan, it should be understood that the above process may be repeated each time the phase galvo changes direction (either positive to negative, or negative to positive). In some embodiments, multiple changes in each direction may occur within a single B-scan, such as with the triangular waveform illustrated in FIG. 6C.

Figure 7:
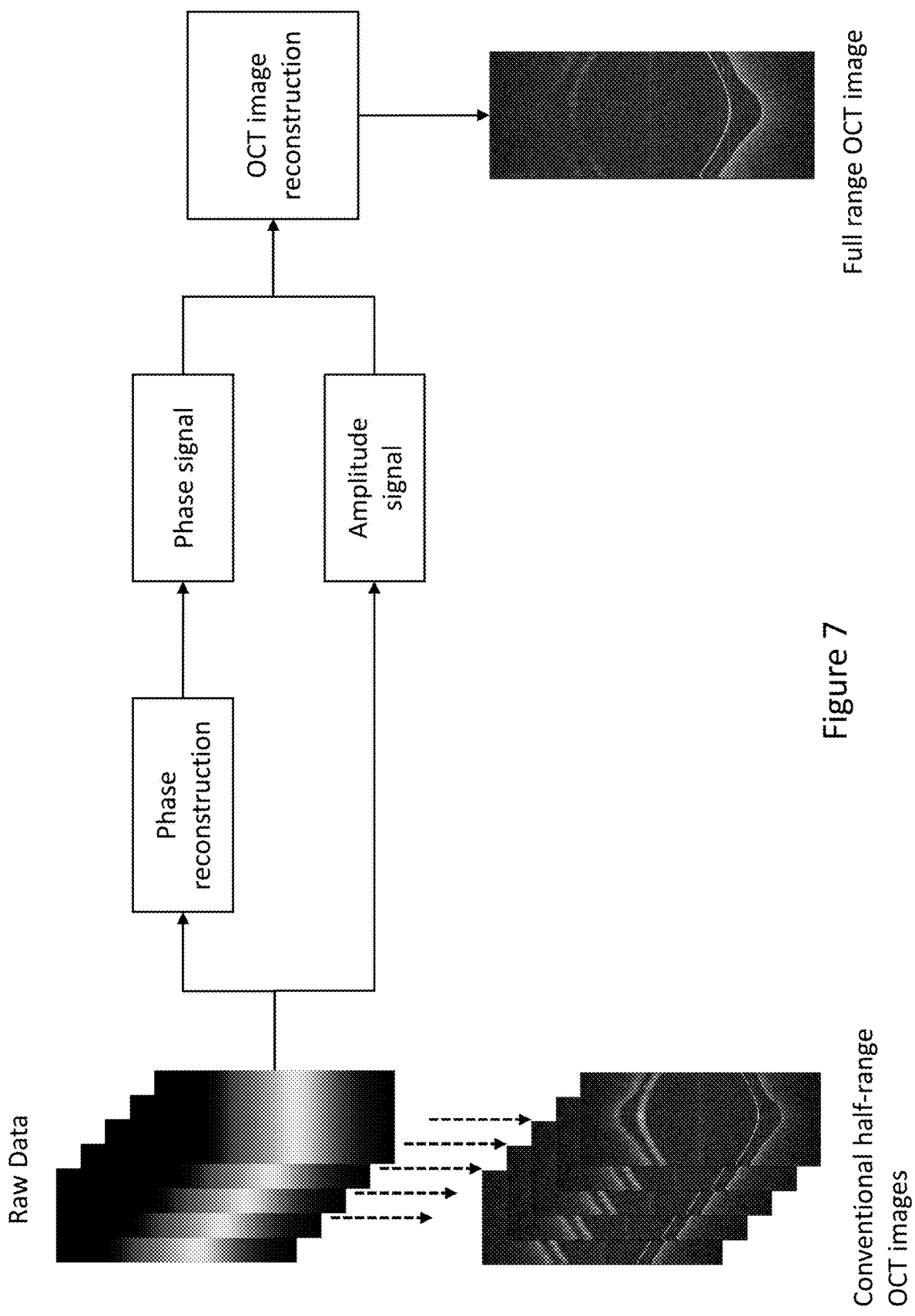
FIG. 7 illustrates a method of reconstructing a full-range OCT image.

Once imaging is complete (after a complete scanning protocol to capture data from all regions of interest of the object), a full-range OCT image can be reconstructed according to the method illustrated in FIG. 7. Briefly, raw intensity data captured by the detector 102 (and which can be used to generate conventional half-range OCT images), which includes the induced phase modulation signal, is processed to reconstruct a phase part of the optical signal. The reconstructed phase part and the amplitude part, also from the raw intensity data, are then both used to reconstruct a full-range OCT image.

According to one embodiment, the phase part may be reconstructed with a multi-element combination technique. Briefly, the technique generates a representative phase signal by combining multiple elements of data (e.g., A-lines or B-scans) into a single representative value. For example, a four element reconstruction technique may combine the data of four adjacent A-lines to generate a phase representative of one of the four combined A-lines.

For any four data elements (e.g., A-lines or B-scans 1-4) having intensities $I_1$-$I_4$, respectively, a representative phase may be given as:

$$\tan(\phi_1) = \frac{I_2 - I_4}{I_1 - I_3}$$

When phase is determined based on more than four data elements, a representative phase is determined for multiple four element subsets. For example, a phase reconstructed from five data elements (e.g., A-lines or B-scans 1-5) would be based on a first four element subset (e.g., A-lines or B-scans 1-4) combined with a second four element subset (e.g., A-lines or B-scans 2-5). The phase for each four element subset follows the format given above. However, where the relative phase between four element subsets is different by π/2 (e.g., where the induced phase modulation signal is adjusted at π/2 intervals between each element), the numerator and denominator of the above phase equation are flipped. Thus, the representative phase for elements 2-5 (or any other set of four elements having a phase offset by π/2) may be given as:

$$\tan(\phi_2) = \frac{I_2 - I_4}{I_3 - I_5}$$

The four element subsets are then combined according to the following:

$$\tan(\phi_2) = \frac{N_1 + N_2}{D_1 - D_2}$$

where N1 and N2 are the numerators of the phases of the first and second four element subsets, respectively; and D1 and D2 are the denominators of the phases of the first and second four element subsets, respectively. Accordingly, the representative phase based on five elements may be given as:

$$\tan(\phi_2) = \frac{N_1 + N_2}{D_1 - D_2} = \frac{I_2 - I_4 + I_2 - I_4}{I_1 - I_3 - (I_3 - I_5)} = \frac{2I_2 - 2I_4}{I_1 - 2I_3 + I_5}$$

The use of additional elements follows the same format, and are shown in Table 1 below.

TABLE 1

Phase reconstruction based on various numbers of elements

| Number of elements (A-lines or B-scans) | Phase ($\phi_n$) |
|---|---|
| 4 | $\tan^{-1}\left(\frac{I_2 - I_4}{I_1 - I_3}\right)$ |
| 5 | $\tan^{-1}\left(\frac{2I_2 - 2I_4}{I_1 - 2I_3 + I_5}\right)$ |
| 6 | $\tan^{-1}\left(\frac{3I_2 - 4I_4 + I_6}{I_1 - 4I_3 + 3I_5}\right)$ |
| 7 | $\tan^{-1}\left(\frac{4I_2 - 8I_4 + 4I_6}{I_1 - 7I_3 + 7I_5 - I_7}\right)$ |
| 8 | $\tan^{-1}\left(\frac{5I_2 - 15I_4 + 11I_6 - I_8}{I_1 - 11I_3 + 15I_5 - 5I_7}\right)$ |
| 9 | $\tan^{-1}\left(\frac{6I_2 - 26I_4 + 26I_6 - 6I_8}{I_1 - 16I_3 + 30I_5 - 16I_7 + I_9}\right)$ |
| 10 | $\tan^{-1}\left(\frac{7I_2 - 42I_4 + 56I_6 - 22I_8 + I_{10}}{I_1 - 22I_3 + 56I_5 - 42I_7 + 7I_9}\right)$ |

With the phase and amplitude information for each B-scan known, the full-range OCT image may be reconstructed. More particularly, the raw intensity data of the multiple elements can then be expressed in a reconstructed complex signal with the numerator of the representative phase being the real part, and the denominator of the representative phase being the imaginary part. Thus, the complex signal based on four elements (A-lines or B-scans) may be given as:

$$D_{complex} = (I_2 - I_4) + i(I_1 - I_3)$$

OCT images may then be generated by applying a Fourier transform to the complex signal, rather than merely the real signal as in conventional techniques.

Figure 8:
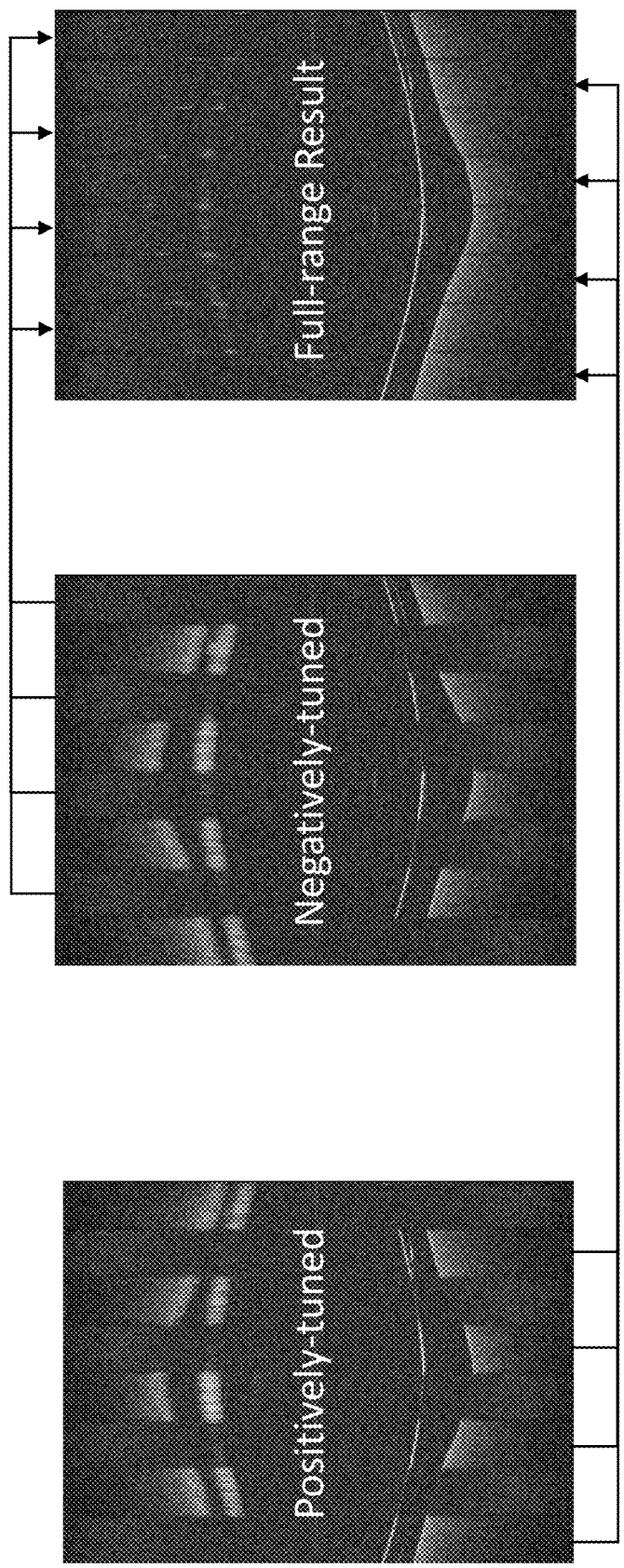
FIG. 8 illustrates positively-tuned and negatively-tuned OCT images stitched together.

To remove artifacts associated with different phase modulations, the tuning direction of the phase modulation signal may be considered. For example, where phase is modulated within a B-scan, the raw intensity data corresponding to a positive tuning direction (an increasing phase delay) is processed as described above with respect to FIG. 7 separately from intensity data corresponding to a negative turning direction (a decreasing phase delay). As illustrated in FIG. 8, such separate processing produces a positively-tuned OCT image and a negatively-tuned OCT image. These images can then be stitched together to produce the final full-range OCT image. The stitching may be performed by combining appropriate A-lines from each of the tuned OCT images.

For example, as seen in FIG. 8, the A-lines associated with the real portion of the image in each tuned OCT image are combined, while the A-lines associated with the mirror image in each tuned OCT image are discarded. The appropriate A-lines to use from each image are known because the relationship between the phase modulation galvo control signal (and thus whether the phase is being positively or negatively tuned) and the fast scanning galvo (indicating the A-line) is known as described above. Any overlapping A-lines (e.g., due to the reversing fast scanning galvo described above with respect to FIG. 6D) may be combined by averaging, using a maximum or minimum, using the positively-tuned A-line, using the negatively-tuned A-lines, or the like. In other embodiments, the imaginary components from one of the positively- or negatively-tuned images are flipped with a dispersion compensation technique.

While various features are presented above, it should be understood that the features may be used singly or in any combination thereof. Further, it should be understood that variations and modifications may occur to those skilled in the art to which the claimed examples pertain.

What is claimed is:

1. An imaging system comprising:
   a light source and a spectrometer in an interferometric arrangement;
   scanning optics configured to scan an object being imaged by the interferometric arrangement along a fast scanning axis;
   a phase modulator configured to adjust a phase of light detected by the spectrometer by inducing a positive phase modulation that increases the phase and inducing a negative phase modulation that decreases the phase; and
   a processor configured to:
      reconstruct a phase of a signal detected by the spectrometer based on the adjusted phase, and
      generate a full-range image based on an amplitude of the signal detected by the spectrometer and the reconstructed phase,
   wherein the positive phase modulation and the negative phase modulation are each induced at least once during a single B-scan, and
   wherein the scanning optics are configured to repeat a scan of a portion of the object along the fast scanning axis when the phase modulator changes between inducing the positive phase modulation and the negative phase modulation.

2. The imaging system of claim 1, wherein the phase modulator is controlled according to a triangular waveform.

3. The imaging system of claim 1, wherein the phase modulator is a phase galvo comprising a rotatable glass.

4. The system of claim 3, wherein the glass is configured to rotate linearly during at least part of a B-scan.

5. The system of claim 4, wherein the glass is configured to rotate during the B-scan according to a triangular waveform.

6. The system of claim 1, wherein the phase modulator is a photonic integrated circuit.

7. The system of claim 1,
   wherein the processor is configured to separately reconstruct the phase of the signal detected by the spectrometer based on the induced positive phase modulation and the induced negative phase modulation, thereby generating a positively-tuned image and a negatively-tuned image, and
   wherein the processor is configured to generate the full-range image by combining the positively-tuned image and the negatively-tuned image.

8. The system of claim 1, wherein the phase modulator is in a sample arm of the interferometric arrangement.

9. The system of claim 1, wherein the phase modulator is in a reference arm of the interferometric arrangement.

10. The system of claim 1, wherein the phase modulator is configured to adjust the phase by $\pi/2$ between each A-line of the single B-scan.

11. An imaging method comprising:
    scanning an object with an incident light with an interferometric imaging system along a fast scanning axis;
    optically modulating a phase of an interference signal from the interferometric imaging system;
    repeating the scan of a portion of the object along the fast scanning axis when the modulated phase changes between a positive phase modulation and a negative phase modulation;
    detecting the optically modulated interference signal;
    reconstructing a phase of the detected signal based on the modulated phase by determining a representative phase based on at least four A-lines or B-scans; and
    generating a full-range image based on an amplitude of the detected signal detected and the reconstructed phase.

12. The imaging method of claim 11,
    wherein optically modulating the phase comprises inducing a positive phase modulation and a negative phase modulation in a single B-scan,
    wherein the phase is separately reconstructed based on the positive phase modulation and the negative phase modulation adjusted phase,
    wherein the method further comprises generating a positively-tuned image based on the reconstructed phase of the positive phase modulation, and generating a negatively-tuned image based on the reconstructed phase of the negative phase modulation, and
    wherein generating the full-range image comprises combining the positively-tuned image and the negatively-tuned image.

13. The imaging method of claim 11, wherein optically modulating the phase comprises inducing a by $\pi/2$ phase between each A-line and/or B-scan.

14. The imaging method of claim 11, wherein optically modulating the phase comprises rotating a phase galvo according to a triangular waveform.

15. The imaging method of claim 11, wherein optically modulating the phase comprises switching light paths through a photonic integrated circuit.

16. The imaging method of claim 11,
    wherein generating the full-range image comprises performing a Fourier transform on a complex signal,
    wherein a real part of the complex signal is represented by at least two of the at least four A-lines or B-scans, and an imaginary part of the complex signal is represented by a different at least two of the at least four A-lines or B-scans, and
    wherein the A-lines or B-scans representing the real and imaginary parts of the complex signal are determined based on the reconstructed phase.

* * * * *